(12) United States Patent
Eck et al.

(10) Patent No.: US 7,742,639 B2
(45) Date of Patent: Jun. 22, 2010

(54) DATA SET VISUALIZATION

(75) Inventors: Kai Eck, Aachen (DE); Alexandra Groth, Aachen (DE); Gundolf Kiefer, Aachen (DE); Helko Lehmann, Aachen (DE); Jorg Bredno, Aachen (DE); Jurgen Weese, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 919 days.

(21) Appl. No.: 10/599,864

(22) PCT Filed: Apr. 11, 2005

(86) PCT No.: PCT/IB2005/051186

§ 371 (c)(1),
(2), (4) Date: Oct. 12, 2006

(87) PCT Pub. No.: WO2005/101277

PCT Pub. Date: Oct. 27, 2005

(65) Prior Publication Data

US 2007/0161892 A1 Jul. 12, 2007

(30) Foreign Application Priority Data

Apr. 16, 2004 (EP) .................................. 04101579

(51) Int. Cl.
*G06K 9/34* (2006.01)
(52) U.S. Cl. ...................................... 382/173
(58) Field of Classification Search ................ 382/100, 382/128, 130–131, 173, 190, 312; 378/21, 378/901; 600/425–429, 439, 101
See application file for complete search history.

(56) References Cited

U.S. PATENT DOCUMENTS

| 6,348,058 | B1 | 2/2002 | Melkent |
| 6,470,207 | B1 | 10/2002 | Simon |
| 7,286,695 | B2 * | 10/2007 | Romsdahl et al. ........... 382/131 |
| 7,542,622 | B1 * | 6/2009 | Angelini et al. ............. 382/275 |
| 2002/0114518 | A1 | 8/2002 | Wilt |

FOREIGN PATENT DOCUMENTS

| EP | 1088524 A1 | 4/2001 |
| EP | 1323380 A2 | 7/2003 |
| WO | 9916352 A1 | 4/1999 |
| WO | 03030738 A1 | 4/2003 |

OTHER PUBLICATIONS

Wei, Z et al., "Robot-Assisted 3D-TRUS Guided Prostate Brachytherapy: System Intergration and Validation", Medical Physics, vol. 31, No. 3, Mar. 2004.
Ding, M. et al., "A Real-Time Biopsy Needle Segmentation Technique using Hough Transform", Medical Physics, vol. 30, No. 8, Aug. 2003.
Fenster, A. et al., "Three-Dimensional Ultrasound Imaging", Physics in Medicine and Biology, vol. 46, No. 5, May 2001.

* cited by examiner

*Primary Examiner*—Jose L Couso

(57) ABSTRACT

In real-time three-dimensional imaging the choice of the visualization method and orientation is crucial for intervention success. The key question is what to ignore and what to show in real-time applications, where user control is not appropriate. An intervention (caused by a user) to an object of interest is visualized without the requirement of an interactive input by the user. Parameters for a visualization procedure are automatically chosen during data acquisition which may allow for an efficient tracking of the actual orientation and relative position of the structure with respect to the object of interest.

17 Claims, 4 Drawing Sheets

DATA SET VISUALIZATION

The present invention relates to the field of digital imaging. In particular, the present invention relates to a method of visualizing a multi-dimensional data set, to an image processing device, to imaging systems and to a computer program for performing a visualization of a multi-dimensional data set.

Both endoscopy and biopsy are important techniques in medical diagnosis. It is often only possible to determine the origin of a symptom or a sign of an early phase of disease by visually examining the inside of the living human body or by taking tissue probes from the inside of the living human body. Every year thousands of endoscope procedures are carried out. Optical endoscopy is a medical procedure used to examine hollow organs or a cavity inside a human body. This is often a painful operation in which the endoscope is inserted into the patient through a natural hole or through a small incision.

During such an examination, a medical procedure may be performed which, for diagnostic treatment purposes, removes a sample of an object of interest, such as a piece of tissue of a specific internal organ by inserting a medical device into the patient's body and, at the same time, monitoring the movement of the medical device by means of, e.g., an ultrasound imaging system. In such real-time three-dimensional imaging, the choice of the visualization method and orientation is crucial for the intervention success. In contrast to non-real time tasks, where the volume may be displayed over and over again in review mode, in real-time tasks there is only one chance to display the volume in the most useful manner.

Volume display is a challenging task due to the large amount of three-dimensional information that has to be displayed on a screen in two dimensions. All visualization methods of three-dimensional data ignore much of the acquired information. For example, with surface shading many image voxels are hidden in the image, which is displayed on the screen. Similarly, the maximum intensity projection, on each projected ray only the contribution of one voxel is displayed.

One question occurring is what to ignore and what to show in real-time applications, since user control may not be possible or may put an undue burden on the user, since the physician is fully concerned with operating his interventional devices.

It is an object of the present invention to provide for improved visualization of multi-dimensional data sets.

According to an exemplary embodiment, the above object may be solved by a method of visualizing an multi-dimensional data set. The method comprises the steps of performing a segmentation of a structure in the data set and performing a visualization of the data set. A projection direction of the visualization is determined on the basis of the structure.

In other words, a structure in a data set may be identified by a segmentation procedure and, depending on the segmented structure, an image slice or projection of the data set is visualized. The position of the projection inside the data set is related to the structure.

Advantageously, according to this exemplary embodiment, this may allow for an automated choice of parameters of the visualization procedure and therefore for an improved visualization.

According to another exemplary embodiment, the visualization is performed on the basis of visualization parameters which comprise information about the projection direction and which are determined on the basis of at least one of the segmentation of the structure in the data set and low-level analysis of the data set. Furthermore, the visualization parameters are selected from the group including a relative position of the structure, a direction relative to the structure, a distance between the structure and an object of interest, a motion estimation, and a motion compensation.

Advantageously, according to this exemplary embodiment, image slices may be visualized in a certain direction relative to the structure and, for example, at a certain distance from the structure. Furthermore, according to this exemplary embodiment, the multi-dimensional data set may comprise data relevant for motion estimation or compensation, such as, for example, electro-cardiogram (ECG) data. This additional data may be used, e.g., for a motion compensated visualization of the data set.

According to another exemplary embodiment, the structure is one of a biopsy needle and an endoscope probe, wherein a first projection of the data set is performed in a direction of a longitudinal axis of the structure, resulting in a first image with an image surface area perpendicular to the direction of the longitudinal axis. Furthermore, a second projection of the data set is performed in a direction perpendicular to the longitudinal axis of the structure, resulting in a second image comprising the structure.

Advantageously, according to this exemplary embodiment, this may provide for a first image slice visualizing a viewing direction of a biopsy needle and a second image slice visualizing the biopsy needle itself and data on a plane comprising the biopsy needle. This may allow for an effective visualization of information required for performing a successful and fast biopsy or endoscopy.

In another exemplary embodiment, at least one of the visualization parameters is displayed during visualization of the data set.

Advantageously, this may provide a physician operating a biopsy needle or an endoscope with important information about, for example, the relative position of the structure with respect to an object of interest.

According to another exemplary embodiment, the method further comprises the step of varying a rendering method in an image resulting from the visualization of the data set. The variation of the rendering method causes a non-uniform quality of the image. Furthermore, according to an exemplary embodiment, the variation of the rendering method comprises a variation of a sampling rate in the image and the variation of the rendering method is performed on the basis of the visualization parameters.

Advantageously, this may allow for maximum image quality in the center of an image slice (where the biopsy needle may be pointed to), and, at the same time, for a reduced image quality at the edges of the image slice (which are not of high interest to the user). Advantageously, this may provide for a reduction of computational cost.

According to another exemplary embodiment, the segmentation is performed on the basis of one of a Hough Transform and a determination of active localizers.

This may allow for an effective and reliable segmentation of the structure.

According to another exemplary embodiment, the data set is acquired by means of an ultrasound imaging system, a CT imaging system and an MR imaging system.

According to another exemplary embodiment of, an image processing device for visualizing a multi-dimensional data set is provided, comprising a memory for storing the data set and an image processor adapted for performing the following operation: loading the data set; performing a segmentation of a structure in the data set; and performing a visualization of the data set. The projection direction of the visualization is determined on the basis of the structure.

Advantageously, this may allow for an improved visualization.

According to another exemplary embodiment, an imaging system includes a memory for storing a multi-dimensional data set and an image processor adapted for performing a visualization of the data set. According to an aspect, the imaging system is one of an MR imaging system, a CT imaging system, and an ultrasound imaging system.

Advantageously, this may allow for an improved visualization of a multi-dimensional data set acquired by a CT imaging system, an MR imaging system or an ultrasound imaging system.

According to another exemplary embodiment, a computer program may, for example, be executed on a processor, such as an image processor. Such computer programs may be part of, for example, a CT scanner system, an MR scanner system or an ultrasound imaging system. These computer programs may be preferably loaded into working memories of image processors or general purpose computers. The image processors are thus equipped to carry out exemplary embodiments of the methods of the present invention. The computer programs may be stored on a computer readable medium, such as a CD-ROM. The computer programs may also be presented over a network, such as the World Wide Web and may be downloaded into the working memory of an image processor from such networks. The computer program according to this exemplary embodiment of the present invention may be written in any suitable programming language, such as C++.

According to an exemplary embodiment, an intervention (caused by a user) to an object of interest is visualized without the requirement of an interactive input by the user, which may be a physician. In fact, parameters for a visualization procedure, such as, e.g., of viewing direction, may be automatically chosen during data acquisition which may allow for an efficient tracking of the actual orientation and relative position of a structure, such as a biopsy needle, with respect to the object of interest, such as, for example, a cyst inside the abdomen or a plastoma or neoplasm inside the uterus of a patient.

These and other aspects of the present invention will become apparent from and elucidated with reference to the embodiments described hereinafter.

Exemplary embodiments of the present invention will be described in the following, with reference to the following drawings.

Figure 1:
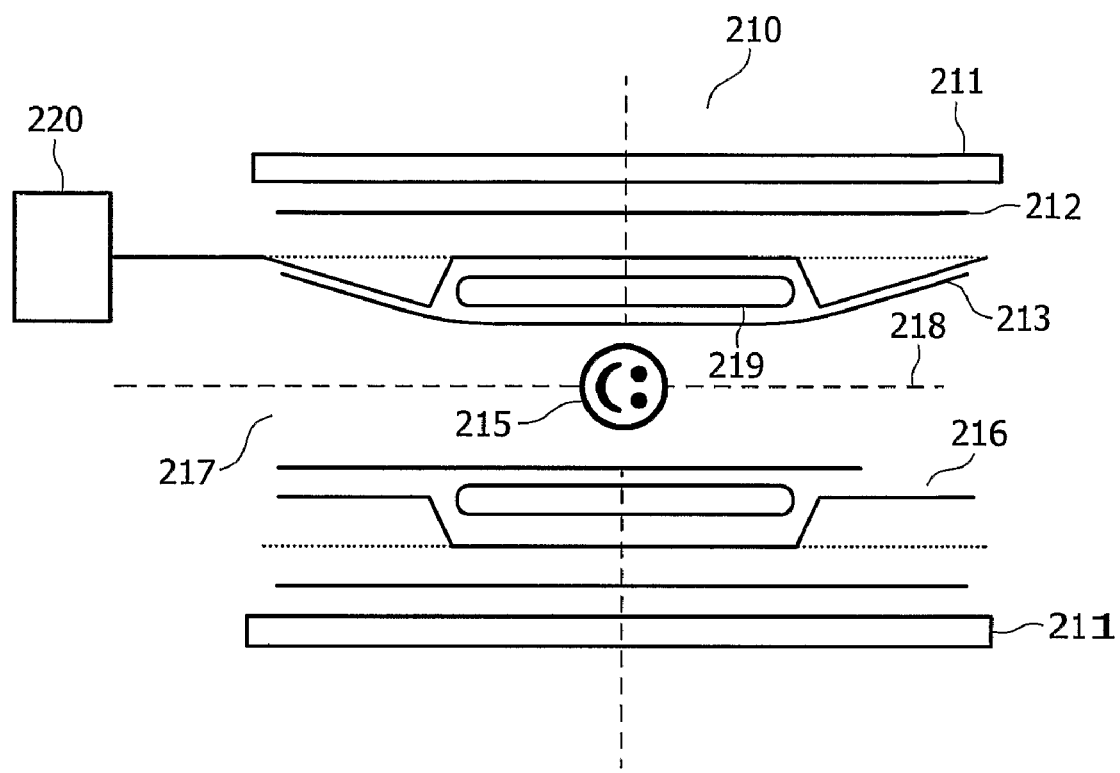
FIG. 1 shows a simplified schematic representation of an embodiment of a magnetic resonance (MR) imaging system according to an exemplary embodiment.

FIG. 1 shows an exemplary embodiment of an MR imaging system. With reference to this exemplary embodiment and to the embodiment depicted in FIG. 2 (ultrasound imaging system), the present invention will be described for the application in the field of medical imaging. However, it should be noted that the present invention is not limited to the application in the field of medical imaging, but may be used in other applications, such as, for example, any other form of minimal invasive procedures which may arise, for example, in the field of baggage inspection to detect hazardous material, such as explosives, in items of baggage or other industrial applications, such as material testing.

The MR scanner system comprises coils 210 which are arranged along an axis 218 and surround an examination space 217, in which a patient 215 who has to be examined or from whom a tissue probe has to be taken is positioned. Advantageously, the patient lies on a movable table or conveyor belt 216, which is disposed at the lower part of the examination space 217. The system of coils 210 surrounding the examination space 217 comprises an RF-coil 219, an actively shielded arrangement of gradient coils comprising an inner coil 213 and an actively shielded coil or shield 212 and a cryostat 211, in which the coils are arranged in order to be cooled down during generation of the magnetic field. The arrangement of gradient coils 213, 212 may be connected to a gradient amplifier 220.

Furthermore, the MR scanner or imaging system may comprise a motor control unit with respective motors, for example, for moving the conveyor belt 216, in the calculation unit (not shown in FIG. 1).

The calculation unit may be realized by an image processor integrated into an image processing device comprising a memory for storing a data set and may also be adapted to perform a visualization of the data set according to an exemplary embodiment of a method according to the present invention. The data processor or image processor according to an aspect of the present invention may be adapted for loading the data set for performing a segmentation of a structure in the data set. Furthermore, the data processor may be adapted for performing a visualization of the data set, wherein a projection direction of the visualization is determined on the basis of the structure.

Furthermore, the calculation unit may be connected to a loudspeaker (not depicted in FIG. 1) to, for example, automatically output of an alarm.

Figure 2:
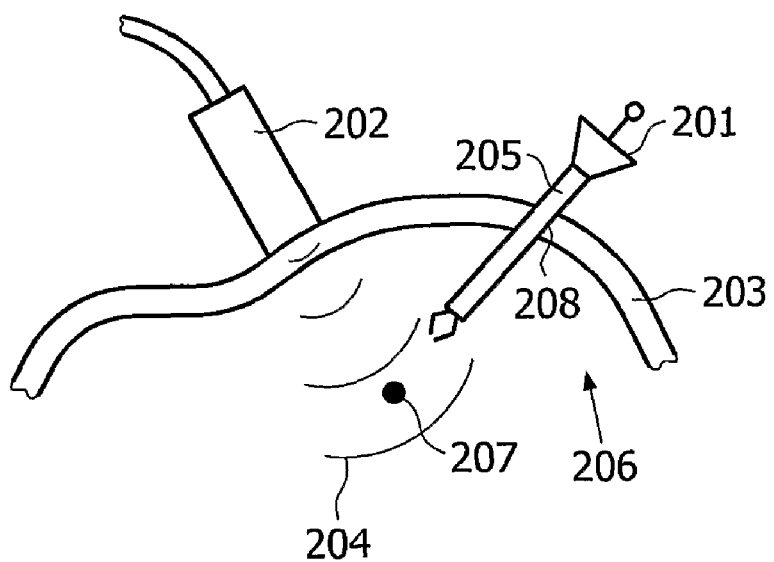
FIG. 2 shows a schematic representation of an interventional biopsy visualized by an ultrasound imaging system according to an exemplary embodiment.

FIG. 2 shows a schematic representation of an interventional biopsy visualized by an ultrasound imaging system according to an exemplary embodiment of the present invention. A biopsy needle 205 is inserted into the patient through a small incision 208 in order to take a tissue sample from the abdomen 206. Biopsy needle 205 may be operated by operating means 201 for cutting a piece of tissue probe 207 from the abdominal wall. In order to track the movement of the biopsy needle 205 and its relative position, with respect to the object of interest 207, an ultrasound imaging system 202 may be employed, according to an exemplary embodiment of the present invention. The ultrasound imaging system 202 may comprise an ultrasound transducer used for generating ultrasound signals 204 propagating towards the object of interest 207 and to receive echo signals reflected from the object of interest 207. Such ultrasound imaging systems are well-known in the art and will not be described here in greater detail.

It should be understood, that the imaging system 202 does not necessarily have to be an ultrasound imaging system but may be any other appropriate kind of imaging system, such as, for example, an MR imaging system or a CT imaging system.

In any case, the imaging system 202 provides for the acquisition of a multi-dimensional data set of the object of interest 207. During the operation the multi-dimensional data set may be constantly updated. The multi-dimensional data set may be a three-dimensional data set representing the volume of the abdomen, or a four-dimensional data set, comprising additional information, where, for example, a heart rate by means of an electro-cardiogram for motion detection and motion compensation. Furthermore, it may also be, for example, a four-dimensional data set formed by a succession of three-dimensional data sets. But it should be understood that the present invention is not limited to three-dimensional or four-dimensional data sets, but as well may be implemented for visualization of five-dimensional or even higher dimensional data sets comprising information beyond the scope of three-dimensional volume information and ECG information.

Somewhere in the volume acquired by the ultrasound imaging system, the biopsy needle is present. Displaying the surfaces of the organs may not help at all, since the needle may be hidden in an organ. Standard projections through the volume can be faint impressions about the direction of the needle relative to the point where the tissue has to be extracted.

The method according to an aspect of the present invention now segments the biopsy needle from the volume, advantageously in real-time, using volume processing methods like a Hough Transform. This segmentation may give the position and elongation direction of the biopsy needle. If the volume is more projected in the direction of the needle elongation, it is instantly clear that a needle targets the centre of interest or not. At the same time, a section through the volume with the needle lying in the display slice may give information about the distance from the needle tip to the target region.

It should be noted that the concept may be extended to a thick slab orientation, choice of surface rendering viewpoint and an integration of active localizers. For example, the segmentation does not necessarily have to be performed by a Hough Transform, which is a computer vision algorithm that can robustly detect a wide variety of features such as lines, circles and anything else that can be readily parameterized or otherwise cast in terms of a discrete popularity algorithm. If, for example, the structure is linear in shape, but not visible to the imaging system, since, for example, some of its physical properties are similar to physical properties of the surrounding tissue (for example a reflection coefficient), it may not be advantageous to use a Hough Transform for segmentation. Instead, active localizers may be integrated in the structure (e.g. biopsy needle) and the integrated active localizers may be individually segmented by means of an alternating external electromagnetic field and an appropriate detector. The detection of active localizers is well-known and will not be described here in greater detail. After detection of integrated active localizers, the orientation and position of the structure may easily be performed.

Figure 3:
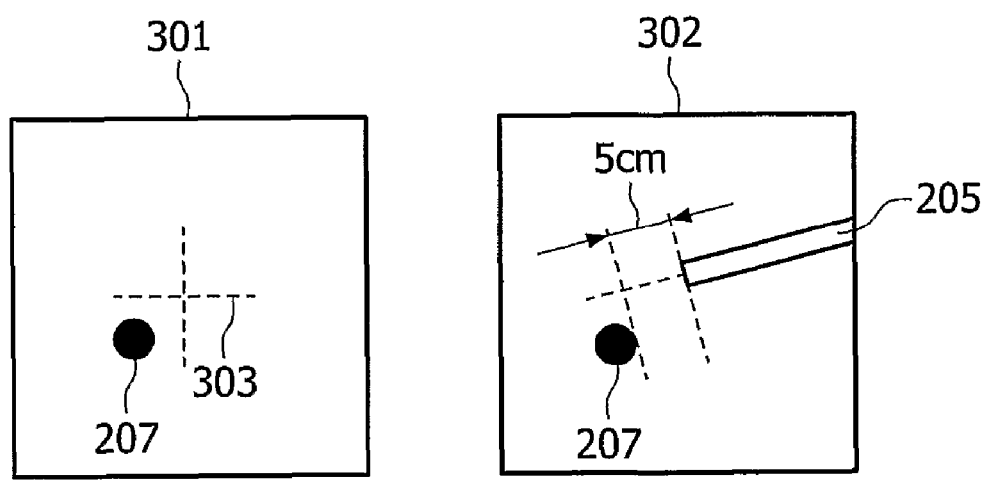
FIG. 3 shows a schematic representation of projections visualized according to an exemplary embodiment.

FIG. 3 shows a schematic representation of two projections visualized according to an exemplary method according to the present invention. The first projection or image slice 301 depicts the object of interest 207 inside the abdominal cavity. Image slice 301 is projected in the direction of the biopsy needle 205 (see FIG. 2), therefore giving the user an idea what the biopsy needle 205 is aiming at. The aim of the biopsy needle 205 may be represented by cross 303.

Image slice 302 represents the object of interest 207 (e.g. a cyst, abscess or neoplasm) and the biopsy needle 205. Since the image slice 302 is taken in the plane of the biopsy needle 205, the distance between the tip of the biopsy needle 205 and the object of interest 207 may be calculated from the data set and displayed on the image slice (here: 5 cm). Both image slices 301 and 302 may effectively aid the physician during the biopsy, therefore, allowing for a fast execution of the biopsy and an accurate extraction of tissue from the object of interest 207.

Figure 4:
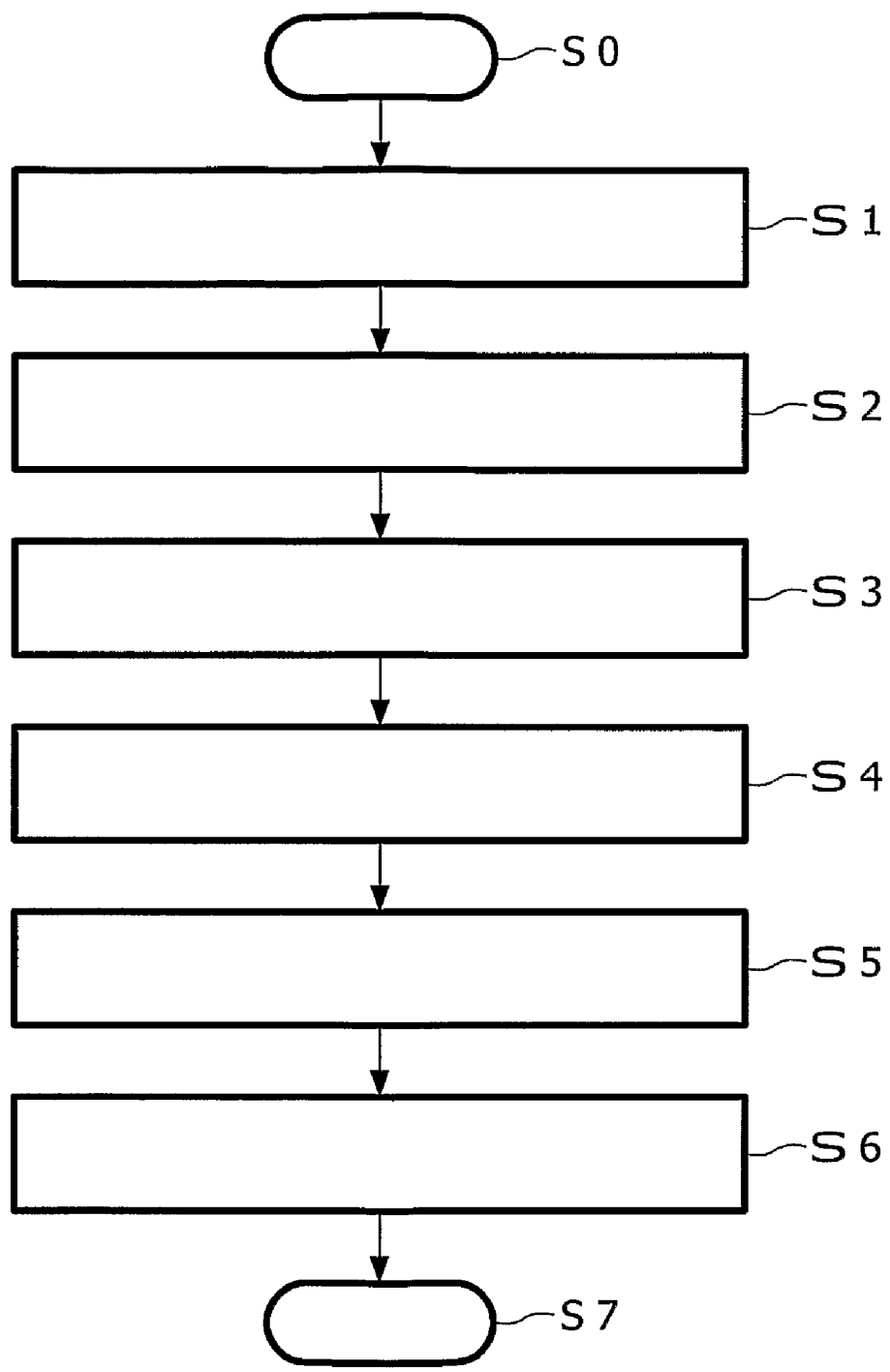
FIG. 4 shows a flow-chart of an exemplary embodiment of a method of visualizing a multi-dimensional data set according to an exemplary embodiment.

FIG. 4 shows a flow-chart of an exemplary embodiment of a method of visualizing a multi-dimensional data set according to the present invention. The method starts at step S0, after which an acquisition of a data set is performed in step S1, for example, by means of a polychromatic source of electromagnetic radiation generating a polychromatic beam and by means of a radiation detector detecting the polychromatic beam, which is the case in, for example, CT imaging.

After that, in step S2 a segmentation of the biopsy needle is performed on the basis of a Hough Transform or a detection of integrated active localizers. Then, in step S3, a low-level analysis of the data set is performed and visualization parameters are selected. The visualization parameters may comprise a relative position of the structure with respect to the object of interest, a direction relative to the structure, a distance between the structure and the object of interest and a motion estimation and compensation on the basis of, for example, ECG-data. The motion may be compensated by a generation of a motion map and performing a motion compensated reconstruction of the image slice on the basis of the motion map. Motion estimation and compensation is well-known in the state of the art and will not be described here in greater detail.

The visualization S4 of the data set comprises a first projection of the data set in a direction of a longitudinal axis of the biopsy needle, resulting in an image slice with an image surface area perpendicular to the longitudinal axis and a second projection in a direction perpendicular to the longitudinal axis of the biopsy needle, resulting in a second image slice comprising the biopsy needle.

In other words, particular selected image slices from the data set are visualized during the examination or operation of the patient. The image slices are selected automatically by the ultra sound imaging system without the need of input from the physician. Advantageously, the image slices represent projections in the view direction of the biopsy needle and in a direction perpendicular to the view direction of the biopsy needle. Therefore, the physician always "looks" in the direction of his biopsy needle 205 independent from its actual position relative to the ultra sound source 202 (see FIGS. 2 and 3).

During rendering of the first and second projections of the data set in step S5, the rendering method in the image slices may be varied, resulting in a non-uniform quality of the image. The variation of the rendering method may comprise a variation of a sampling rate of the images or projections of the data sets on the basis of the visualization parameters. For example, the area adjacent to the cross 303 in FIG. 3 may be rendered with a high sampling rate, resulting in a maximum image quality in the centre of the image slice 301, wherein the outer area of image slice 301 may be rendered with a lower sampling rate, resulting in a lower image quality at the edges of the image slice 301. Therefore, important parts of the image 301 (namely the centre) are displayed in high image quality, whereas parts of lower interest (the outer areas) are represented with lower image quality, therefore, resulting in a reduction of computational costs and improved rendering speed.

After that, in step S6, parameters based on a low-level analysis of the data set, such as, for example, the distance between the structure and the object of interest, are displayed during visualization of the data set.

The method ends at step S7.

Figure 5:
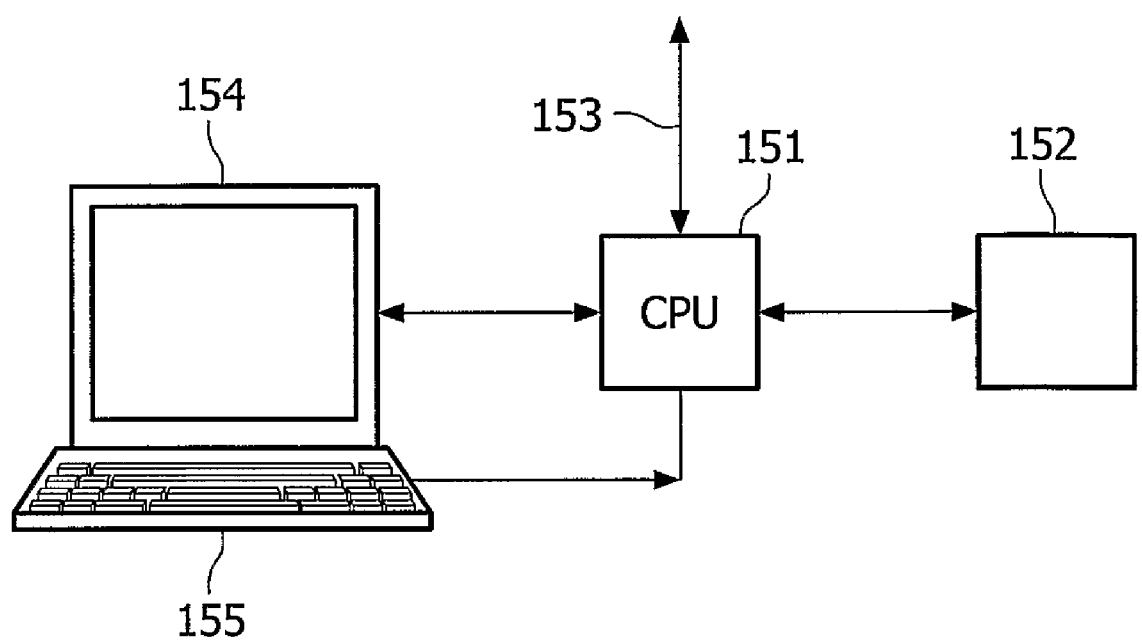
FIG. 5 shows an exemplary embodiment of an image processing device for executing an exemplary embodiment of a method.

FIG. 5 depicts an exemplary embodiment of an image processing device according to the present invention for executing an exemplary embodiment of a method in accordance with the present invention. The image processing device depicted in FIG. 5 comprises a central processing unit (CPU) or image processor 151 connected to a memory 152 for storing an image depicting an object of interest, such as a piece of tissue of a patient's body. The image processor 151 may be connected to a plurality of input/output network or diagnosis devices, such as an MR device or an ultrasound imaging system. The image processor is furthermore connected to a display device 154, for example, a computer monitor, for displaying information or an image computed or adapted in the image processor 151. An operator may interact with the image processor 151 via a keyboard 155 and/or other output devices, which are not depicted in FIG. 5.

Furthermore, via the BUS system 153 it is also possible to connect the image processing and control processor 151 to, for example, a motion monitor which monitors a motion of the object of interest. In case, for example, a lung of a patient is subject to the biopsy or an endoscopy, the motion sensor may be an exhalation sensor. In case the heart is imaged, the motion sensor may be an electrocardiogram (ECG).

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A method of visualizing a multi-dimensional data set, the method comprising:
   with one or more processors, performing a segmentation of a structure in the data set; and
   with one or more processors, performing a visualization of the data set, the visualization being performed on the basis of visualization parameters comprising a projection direction, the visualization parameters being determined on the basis of at least one of the segmentation and a low-level analysis of the data set and the visualization parameters being selected from a relative position of the structure, a direction relative to the structure, a distance between the structure and an object of interest, a motion estimation, and a motion compensation;
   wherein a projection direction of the visualization is determined on the basis of the structure.

2. The method according to claim 1, wherein the structure is one of a biopsy needle and an endoscope probe;
   wherein a first projection of the data set is performed in a direction of a longitudinal axis of the structure, resulting in a first image with an image surface area perpendicular to the direction of the longitudinal axis; and
   wherein a second projection of the data set is performed in a direction perpendicular to the longitudinal axis of the structure, resulting in a second image comprising the structure.

3. The method according to claim 2, wherein at least one of the visualization parameters is displayed on a display device during visualization of the data set.

4. The method according to claim 1, further comprising:
   varying a rendering method in an image resulting from the visualization of the data set;
   wherein the variation of the rendering method causes a non-uniform quality of the image.

5. The method according to claim 4, wherein the variation of the rendering method comprises a variation of a sampling rate in the image; and
   wherein the variation of the rendering method is performed on the basis of the visualization parameters.

6. The method according to claim 1, wherein the segmentation is performed on the basis of one of a Hough Transform and a determination of active localizers.

7. The method according to claim 1, wherein the data set is acquired by means of one of an ultrasound imaging system, a CT imaging system, and an MR imaging system.

8. An image processing device for visualizing a multi-dimensional data set, the image processing device comprising:
   a memory for storing the data set;
   an image processor adapted for performing the following operations:
      loading the data set,
      performing a segmentation of a biopsy needle in the data set, and
      performing a visualization of the data set on the basis of visualization parameters, the visualization parameters being determined on the basis of at least one of the segmentation and a low-level analysis of the data set and the visualization parameters being selected from the group including a relative position of the structure, a direction relative to the structure, a distance between the structure and an object of interest, and a motion estimation;
   wherein a first projection of the data set is performed in a direction of a longitudinal axis of the biopsy needle, resulting in a first image with an image surface area perpendicular to the direction of the longitudinal axis; and
   wherein a second projection of the data set is performed in a direction perpendicular to the longitudinal axis of the biopsy needle, resulting in a second image comprising the biopsy needle.

9. An imaging system comprising:
   a memory which stores a multi-dimensional data set;
   an image processor which performs a visualization of the data set, the image processor being programmed to:
      load the data set,
      segment an inserted end of a surgical instrument in the data set, and
      perform a visualization of the data set including performing a first projection of the data set in a direction of a longitudinal axis of the inserted end of the surgical instrument, resulting in a first image with an image surface area perpendicular to the direction of the longitudinal axis and performing a second projection of the data set in a direction perpendicular to the longitudinal axis of the inserted end of the surgical instrument, resulting in a second image including the inserted end of the surgical instrument.

10. The imaging system according to claim 9, wherein the imaging system is one of an MR imaging system, a CT imaging system, and an ultrasound imaging system.

11. A tangible computer readable medium carrying a computer program for controlling one or more processors to perform a visualization of a multi-dimensional data set including:
   loading the data set;
   performing a segmentation of a structure in the data set;
   determining visualization parameters on the basis of at least one of the segmentation and low-level analysis of the data set, the visualization parameters including one or more of a relative position of the structure, a direction relative to the structure, a distance between the structure and an object of interest, a motion estimation, and a motion compensation; and performing a visualization of the data set including projecting the data set in a projection direction based on the visualization parameters.

12. The imaging system according to claim 9, wherein the visualization is performed on the basis of visualization parameters determined on the basis of at least one of the segmentation and a low-level analysis of the data set, the visualization parameters including a relative position of the inserted end of the surgical instrument, a direction relative to the inserted end of the surgical instrument, a distance between the inserted end of the surgical instrument and an object of interest, a motion estimation, and a motion compensation.

13. The imaging system according to claim 9, wherein the surgical instrument is one of a biopsy needle and an endoscopic probe.

14. The computer readable medium according to claim 11, wherein a first projection of the data set is performed in a direction of a longitudinal axis of the structure, resulting in a first image with an image surface area perpendicular to the direction of the longitudinal axis; and wherein a second projection of the data set is performed in a direction perpendicular to the longitudinal axis of the structure, resulting in a second image comprising the structure.

15. An imaging system comprising:

an imaging device that generates image data during an interventional procedure in which an interventional structure is inserted in an imaged object;

an image processor programmed to:
    segment the image data,
    analyze the segmented image data to determine one or more viewing directions based on the interventional structure in the segmented image data without operator input,
    project the segmented data set along the one or more viewing directions; and
a display device on which images of the one or more projected segmented data sets are displayed.

16. The imaging system according to claim 15, wherein the projection directions are based on one or more of a relative position of the interventional instrument, a direction relative to the interventional instrument, a distance between the interventional instrument and a target point in the object, a motion estimation, and a motion compensation.

17. The imaging system according to claim 15, wherein the interventional instrument is one of a biopsy needle and an endoscope probe, and wherein the image processor is further programmed to project the segmented data set along two viewing directions, a first of the viewing directions being in a direction of a longitudinal axis of the biopsy needle or surgical probe and the displayed projected segmentation data representing an image perpendicular to the direction of the longitudinal axis and along a second direction which is perpendicular to the longitudinal axis with the segmented data set projected in the second direction including the biopsy needle or endoscope probe.

* * * * *